United States Patent

Tanner, II

Patent Number: 5,713,875
Date of Patent: Feb. 3, 1998

[54] SYSTEM FOR ADMINISTRATION OF A LIQUID AGENT TO A PATIENT WITH A SYRINGE PUMP

[75] Inventor: John C. Tanner, II, Lake Bluff, Ill.

[73] Assignee: Abbott Laboratories, Abbott Park, Ill.

[21] Appl. No.: 685,266

[22] Filed: Jul. 23, 1996

Related U.S. Application Data

[63] Continuation-in-part of Ser. No. 283,305, Jul. 29, 1994, abandoned.

[51] Int. Cl.$^6$ .................... A61M 5/24; A61M 5/28
[52] U.S. Cl. ............... 604/203; 604/205; 604/201; 604/218; 604/411
[58] Field of Search ............... 604/203, 206, 604/232, 68, 87, 88, 89, 91, 86, 205, 200–202, 218, 411, 414, 415, 905, 181, 107

[56] References Cited

U.S. PATENT DOCUMENTS

| | | | |
|---|---|---|---|
| 3,850,174 | 11/1974 | Ayres | 604/415 |
| 4,169,475 | 10/1979 | Genese | 604/414 |
| 4,182,326 | 1/1980 | Ogle | 604/203 |
| 4,191,225 | 3/1980 | Ogle | 604/414 |
| 4,365,626 | 12/1982 | House | 604/203 |
| 5,019,052 | 5/1991 | Rohrbough | 604/203 |
| 5,380,281 | 1/1995 | Tomellini et al. | 604/203 |

*Primary Examiner*—Michael Powell Buiz
*Assistant Examiner*—Ronald K. Stright, Jr.
*Attorney, Agent, or Firm*—David C. Hannum; Brian R. Woodworth

[57] ABSTRACT

A system is provided for accommodating the use of a syringe pump to inject a liquid agent into a patient from a vial having an internal chamber occluded at one end by a stopper located in the chamber to sealingly engage the vial and slide within the chamber. The system includes a plunger having a bearing end to be engaged by a movable pushing member of the syringe pump and having a drive end adapted to engage the stopper. A hollow piercing needle is mounted to the plunger to be connected in fluid communication with the patient and has a piercing end to penetrate the stopper. The needle moves with the plunger and stopper relative to the chamber as the liquid is discharged from the vial.

5 Claims, 3 Drawing Sheets

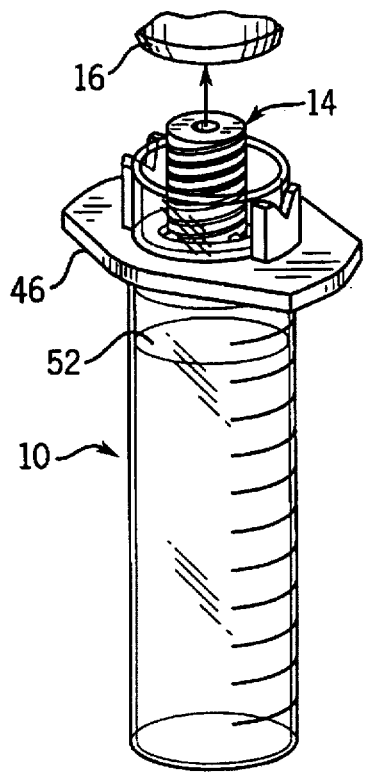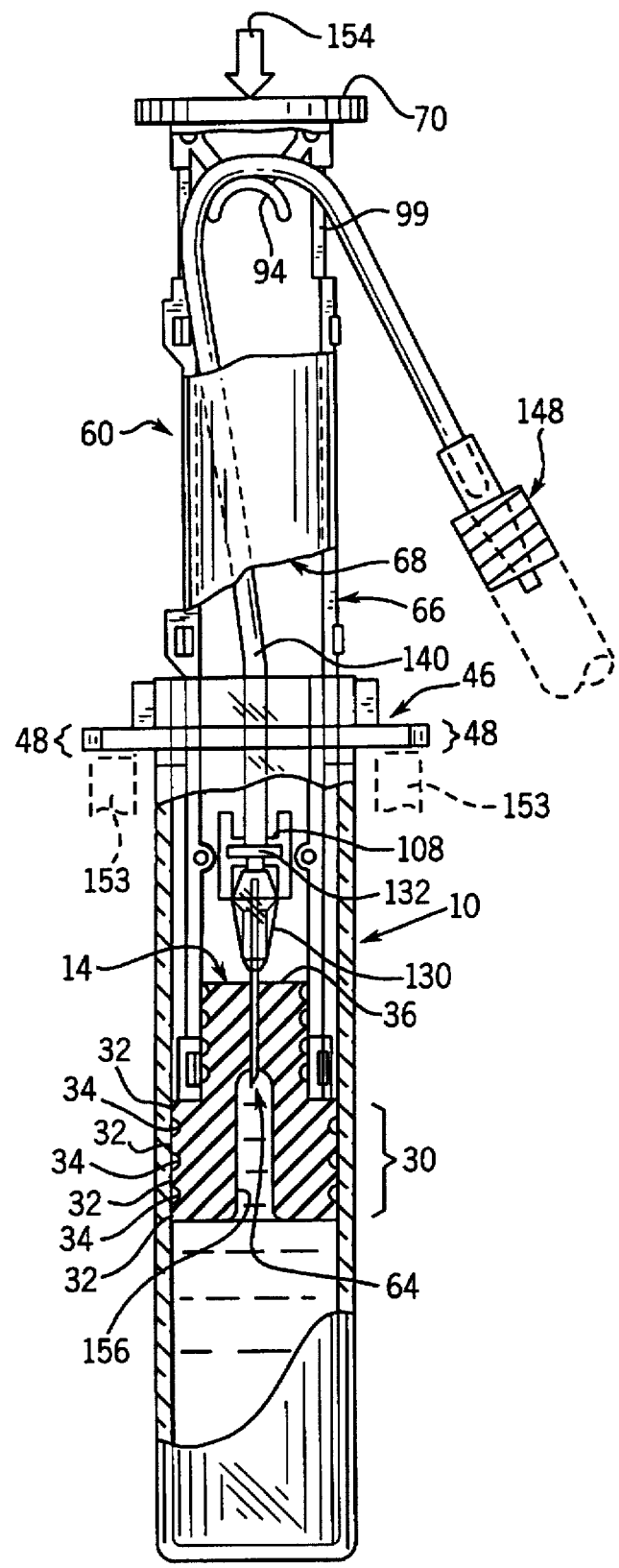

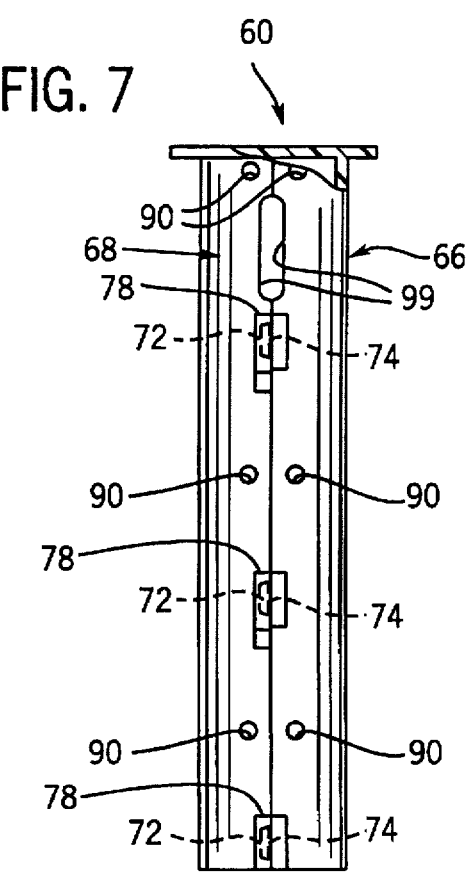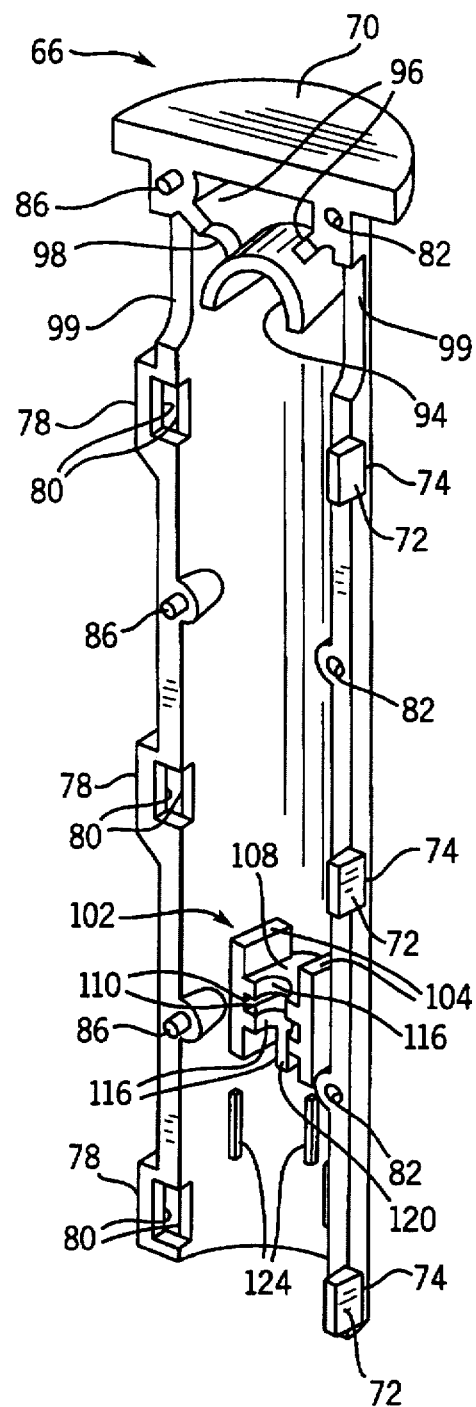

SYSTEM FOR ADMINISTRATION OF A LIQUID AGENT TO A PATIENT WITH A SYRINGE PUMP

This application is a continuation of U.S. Pat. application Ser. No. 283,305, filed Jul. 29, 1994, which is abandoned.

TECHNICAL FIELD

The present invention relates to apparatus for providing a liquid agent to a patient by means of a standard parenteral infusion syringe pump. The apparatus is particularly well-suited for accommodating the intravenous administration of liquids, including drugs.

BACKGROUND OF THE INVENTION AND TECHNICAL PROBLEMS POSED BY THE PRIOR ART

Conventional syringe pumps are typically employed with either a syringe or a vial and plunger system for administering a liquid agent to a patient. In such conventional systems, a syringe or vial of the liquid agent is oriented vertically in a fixed position on the syringe pump. The bottom of the syringe or vial defines a discharge port connected to a flexible, hollow tubing which extends to the patient and which has a suitable cannula at the distal end for insertion into the patient's vein.

The plunger or piston of the apparatus is engaged with the moving pusher plate or drive member of the syringe pump and is driven downwardly into the syringe body or vial to force the liquid agent from the syringe body or vial through the tubing and into the patient.

While such systems function generally satisfactorily, it would be desirable to provide an improved liquid agent container and delivery system. It would also be advantageous if such an improved system could be employed with certain conventional vials and with various conventional syringe pumps, especially the newer syringe pumps which require smaller maximum diameter syringes.

Additionally, it would be desirable if an improved system could provide the capability for purging air from the system while the system apparatus is mounted in the syringe pump in a normal, elevated, vertically oriented position.

It would also be beneficial if such an improved system could accommodate the use of a relatively low-cost glass vial having a single opening.

It would be advantageous if such an improved system could also optionally accommodate the use of plastic vials (especially where plastic/liquid contact is acceptable).

It would also be desirable if an improved system could incorporate a relative low-cost short needle plunger design having a more convenient overall dispensing height or length.

Finally, it would be desirable to provide an improved system that could accommodate designs having a reduced number of closures, such as rubber stoppers, with which the liquid agent is in contact.

The present invention provides an improved system for administration of a liquid agent to a patient with a syringe pump wherein the system can accommodate designs having the above-discussed benefits and features.

SUMMARY OF THE INVENTION

The present invention, in its preferred form, permits the use of a pre-filled and sterilized container (e.g., a glass vial) to be used in a conventional syringe pump. It is especially advantageous for liquid agent products that are only stable in glass containers. However, the present invention may also be employed with plastic containers.

The novel apparatus of the present invention permits the system to be purged of air while it is mounted in the pump in its normal dispensing position. This simplifies the air purging process.

According to one aspect of the present invention, a system is provided for accommodating the use of a syringe pump to inject a liquid agent into a patient from a vial having an internal chamber which is occluded at one end by a stopper located in the chamber to sealingly engage the vial and slide within the chamber.

The system includes a plunger having a bearing end to be engaged by a movable pushing member of the syringe pump. The plunger has a drive end adapted to engage the stopper. The drive end is sized to enter the vial chamber as the stopper is pushed by the plunger while the vial is held stationery in the syringe pump.

A hollow piercing needle is mounted to the plunger. The needle is connected in fluid communication with the patient and has a piercing end which penetrates the stopper. After the needle has penetrated the stopper, the needle subsequently moves with the plunger and stopper relative to the chamber as the liquid is discharged from the vial.

According to another aspect of the present invention, at least one type of conventional vial can be adapted for use with the system by attaching a flange to the vial. The flange engages a stationary receiving structure on the syringe pump.

In a preferred embodiment, tubing is connected to the base of the needle and extends generally upwardly away from, and out of, the top of the vial as the plunger moves further into the vial. The tubing is bent around an upper portion of the plunger and from there extends down to the patient.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIG. 4 is a view similar to FIG. 3, but FIG. 4 shows the cap removed from the flanged vial;

FIG. 5 is a view of the vial of FIG. 4 shown engaged with the dispensing system of the present invention, and FIG. 5 shows portions of the vial cut away to illustrate interior detail and shows portions of one of the components of the dispensing system plunger cut away to illustrate interior detail;

FIG. 6 is a greatly enlarged, perspective view of one piece of the two-piece plunger which is shown in FIG. 5; and FIG. 7 is a reduced, side elevational view of the plunger of FIG. 5 shown in partial cross section to illustrate interior detail.

DESCRIPTION OF THE PREFERRED EMBODIMENTS

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

For ease of description, the components of this invention are described in a typical operating position, and terms such as upper, lower, horizontal, etc., are used with reference to this position. It will be understood, however, that the components of this invention may be manufactured, stored, transported, used, and sold in an orientation other than the position described.

Figures illustrating the apparatus of the invention show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

The components of this invention are used with certain conventional equipment (e.g., a syringe pump, tubing, connectors, etc.) the details of which, although not fully illustrated or described, will be apparent to those having skill in the art and an understanding of the necessary functions of such components.

Figure 1:
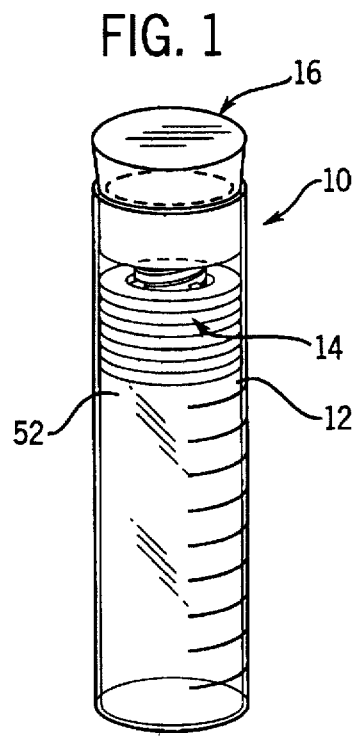
FIG. 1 is a perspective view of a vial containing a liquid agent.

The system of the present invention may be employed in the administration of a liquid agent from a variety of containers. One such container is a vial 10 illustrated in FIG. 1. The vial 10 is a conventional glass vial sold in the U.S.A. as part of the ABBOJECT® brand unit of use packaging systems for use with syringe pumps by Abbott Laboratories, Inc., One Abbott Park Road, Abbott Park, Ill. 60064-3500, U.S.A.

The vial 10 includes a glass cylindrical container 12 having a closed bottom and an open top which is sealed with an internal piston-type stopper 14 and which is additionally covered with a removable cap 16.

Figure 2:
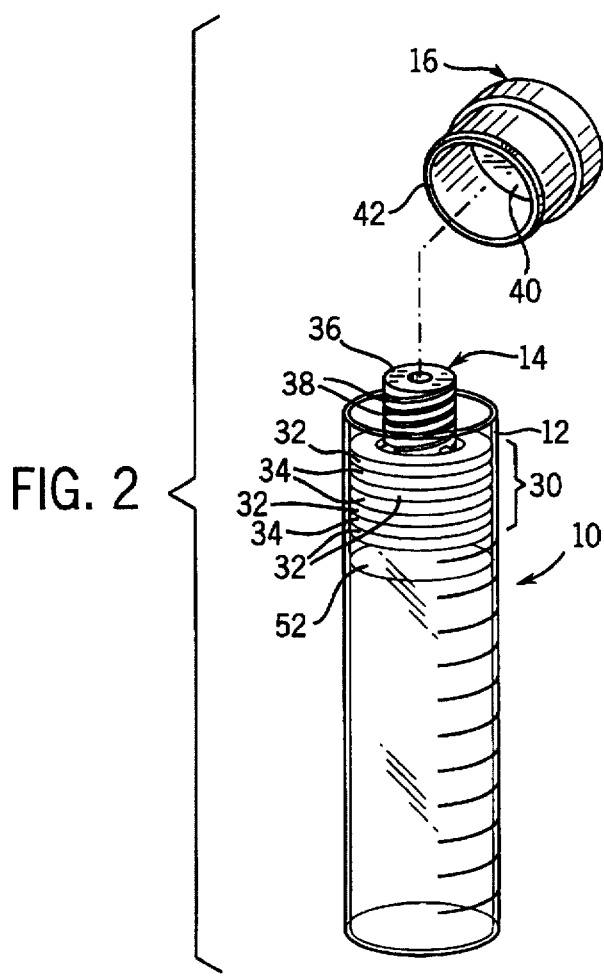
FIG. 2 is a view similar to FIG. 1, but FIG. 2 shows the vial cap removed to expose a stopper having a threaded upper end.

As illustrated in FIG. 2, the stopper 14 includes a resilient, sealing piston portion 30 which is sealingly engaged with the interior circumference of the container 12. The piston portion 30 includes a plurality of rings 32 spaced by grooves 34.

A post 36 projects upwardly from the piston portion 30 and is a unitary part of the stopper 14. The post may include a helical thread 38.

The cap 16 includes a transverse end wall 40 and a reduced diameter lower skirt 42 for being received within the container 12.

Figure 3:
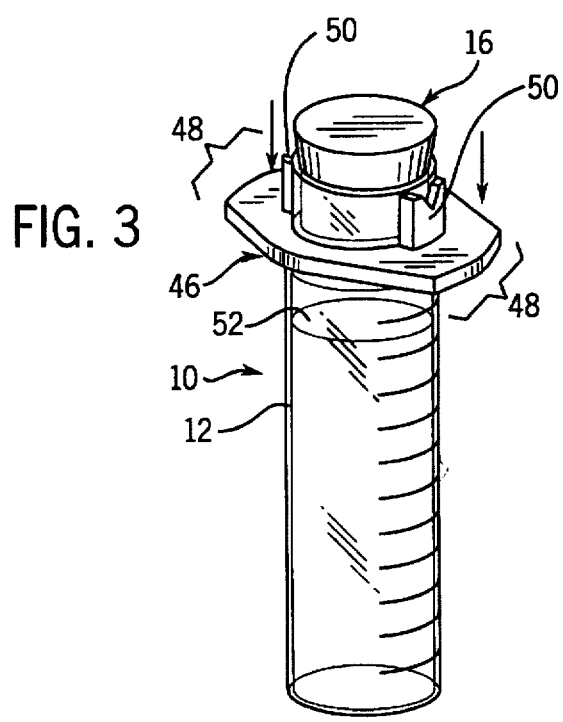
FIG. 3 is a view similar to FIG. 1, but FIG. 3 shows the attachment of a flange to the upper end of the vial.

In a preferred embodiment, the ABBOJECT®brand vial is modified by adding a flange 46 (FIG. 3). The flange 46 can be relatively inexpensively molded for use with the vial 10 or with any other suitable vial or container.

The flange 46 includes a pair of oppositely extending wing portions 48 and a pair of spaced-apart saddle members 50 which provide stability for mounting and attaching the flange 46 to the exterior, cylindrical surface of the vial container 12.

As presently contemplated, the vial 10 is initially prepared at a manufacturing facility by filling the vial with a desired quantity of liquid agent 52 and by subsequently inserting the stopper 14 and cap 16. Then the flange 46 is installed. Any suitable attachment system may be employed.

One contemplated attachment system uses an ultraviolet radiation curable adhesive or epoxy. Proper attachment of the flange 46 does not interfere with subsequent removal of the cap 16 and with subsequent access to the stopper 14.

According to the present invention, the modified vial 10 can be employed with a conventional syringe pump for administering the liquid agent 52 to a patient. To this end, the present invention provides a plunger 60 (FIG. 7) and a hollow piercing needle 64 10 mounted to the plunger. The plunger and needle are adapted to engage the vial 10.

In particular, the plunger 60 includes, in a preferred form, two, identical, molded, thermoplastic pieces 66 and 68 (FIG. 7). The plunger piece 66 is shown greatly enlarged in FIG. 6. The piece 66 has a generally semi-cylindrical configuration with an upper bearing end plate 70. As viewed in FIG. 6, the right-hand vertical edge of the piece 66 includes three latch tabs 72, and each latch tab extends toward the right beyond the cylindrical exterior surface of the piece 66 to define a generally planar latch surface 74 (facing away from the observer as viewed in FIG. 6).

On the left-hand vertical edge of the piece 66 (as viewed in FIG. 6), the piece 66 defines three lugs 78 which extend outwardly (to the left as viewed in FIG. 6) from the cylindrical surface of the piece 66. The lugs 78 each define an aperture 80 for receiving an inserted latch tab 72 of the mating piece 68. The outer edge of each lug 78 extends rearwardly (as viewed in FIG. 6) for a distance which is longer than the depth of the insertion of the tab 72. However, the wall of the lug 78 is undercut adjacent the aperture 80 to provide a ledge for engaging the latch surface 74 of the tab 72.

The right-hand vertical edge of the piece 66 also defines three bores 82, and the left-hand vertical edge of the piece 66 defines three projecting pins 86.

The plunger piece 68 is identical with the plunger piece 66 described above with reference to FIG. 6. When the plunger pieces 66 and 68 are placed together as shown in FIG. 7 to form the generally cylindrical plunger 60, the latch tabs 72 of one piece are received in the apertures 80 of the other piece, and the pins 86 of one piece are received in the bores 82 of the other piece. The latch tabs 72 are sufficiently resilient to accommodate a temporary, inward deformation so that the latch surface 74 of each latch tab 72 passes through the associated aperture 80 and then snaps outwardly behind the lug 78 adjacent the aperture 80 to effect a secure, snap-fit engagement.

The pins 86 may be adhesively secured within the mating bores 82. Alternatively, external heating elements may be applied to an external depression 90 (FIG. 7) behind each bore and pin to effect an interface melting of the thermoplastic material. Subsequent cooling results in a resolidified heat seal bond.

The internal configuration of each plunger piece 66 and 68 is identical. With reference to the plunger piece 66 illustrated in FIG. 6, it is seen that the plunger piece 66 includes a generally transversely oriented, semi-cylindrical guide wall 94. Two angled retaining walls 96 extend outwardly from the top surface of the guide wall 94, and each retaining wall 96 defines a notch 98 for receiving tubing as described hereinafter.

Adjacent the curved surface 94, the sidewall of the plunger piece 66 defines a pair of opposed slots or channels 99. These channels 99 accommodate the extension of connecting tubing (described hereinafter) out of the plunger.

In the lower portion of the plunger piece 66, there is a unitary needle hub mounting structure 102 which includes a pair of spaced-apart, vertically oriented walls 104 (FIG. 6). This receives the needle 64 as described in detail hereinafter. The walls 104 are joined by central cross wall 108 which defines a horizontal groove 110 and a vertical groove 116. A short, vertical, middle wall 120 extends downwardly between the walls 104 from the lower surface of the cross wall 108, and the wall 120 functions as a rigidifying structure.

A plurality of vertical ribs 124 are provided on the interior surface of the plunger piece 66 below the needle hub mounting structure 102.

The needle 64 is mounted in a conventional hub 130 (FIG. 5). The top of the hub 130 terminates in an outwardly extending, horizontal flange 132. The horizontal flange 132 is received in the horizontal groove 110 in the wall 108, and a portion of the hub 130 below the flange 132 is received in the vertical groove 116 below the horizontal groove 110 in the wall 108.

The conventional needle hub 130 is attached to thermoplastic tubing 140 in a well-known manner. The end of the tubing 140 is received within a suitable bore in the hub 130, and the bore communicates with the interior passage of the hollow needle 64 so that fluid communication is established between the needle 64 and the tubing 140.

The tubing 140 extends upwardly from the hub flange 132 and is received within the groove 116 of the transverse wall 108 above the horizontal groove 110. The tubing 140 extends to the top of the plunger pieces 66 and 68. The tubing 140 is positioned around the curved guide wall 94 and in a cooperating pair of the notches 98 (FIG. 6) defined in the walls 96. The tubing 140 extends out of the plunger through the notches 99 (FIG. 5).

The distal end of the tubing 140 is connected in a well-known manner to a luer lock connector fitting 148 or directly without fittings into a fluid administration set connected to a patient. The fitting 148 can be connected to a suitable conventional or special tubing system (not shown) which terminates in a needle or canula for insertion into the patient.

In an alternate embodiment (not illustrated) the tubing 140 could be rigid within the plunger 60 and could terminate at a lateral port near the top of the plunger 60. Flexible tubing could then be connected exterior of the plunger 60 to such a lateral port, and the flexible tubing would then extend down toward the patient.

When the two plunger pieces 66 and 68 are secured together about the needle 64, hub 130, and tubing 140, the hub and needle are securely retained within the plunger 60. Typically, the plunger 60, with the needle mounted therein, and projecting therefrom, is provided to the user with a suitable protective sleeve (not shown) over the projecting distal end of the needle 64. When it is desired to administer the liquid agent from the vial 10 with the assembled plunger 60 and needle 64 in a conventional syringe pump, the protective sleeve (not shown) is removed from the needle.

Next, the cap 16 is removed from the vial 10. The plunger and needle assembly is then pushed onto the top of the vial container 12. The outside diameter of the plunger 60 is less than the inside diameter of the vial container 12, but the inside diameter defined by the plunger pieces 66 and 68 is just large enough to receive the upwardly projecting post 36 of the vial stopper 14.

Preferably, the plunger ribs 124 (FIG. 6) deform the resilient material of the stopper post 36 slightly and establish a friction engagement therewith. As the needle 64 is pushed into the stopper 14, the needle 64 pierces the stopper and completely penetrates the stopper.

As illustrated in FIG. 5, the stopper 14, in a conventional ABBOJECT® brand vial, defines a concave cavity 156 facing downwardly toward the container interior. The distal end of the needle 64 passes completely through the stopper post 36 and enters the cavity within the stopper. The end of the needle 64 is exposed to the container liquid agent. The bottom ends of the plunger pieces 66 and 68 engage the larger diameter stopper seal piston 30.

Initially, when the plunger and needle are first engaged as described above with the stopper at the top of the container, the ribs 124 on the inside of the plunger pieces 66 and 68 provide sufficient frictional engagement to permit further handling without the vial and plunger being inadvertently pulled apart.

The assembly is installed in the conventional syringe pump with the vial 10 in the location normally occupied by a hypodermic syringe body. The flange 48 is engaged with the syringe pump stationery structure (shown in phantom in FIG. 5 as elements 153). The bearing plate 70 at the upper end of the plunger (FIG. 6) is adapted to be engaged with the movable drive member or pusher plate of the syringe pump (indicated schematically in FIG. 5 by arrow 154). The syringe pump pusher plate is typically driven by a slowly rotating, fine-threaded screw drive so as to move the plunger further inwardly into the vial 10. Because the bottom of the plunger 60 is engaged with the top of the vial stopper seal piston 30, movement of the plunger 60 into the vial 10 necessarily slides the stopper 14 further into the vial. This forces the liquid agent through the needle 64 and tubing 140 to the patient.

Conventional syringe pumps are typically hung in an elevated orientation from a stand adjacent the patient's bed. The moving pusher plate of the syringe pump is located vertically above the plunger, and the plunger is located vertically above the vial 10. With the system of the present invention, this type of orientation accommodates the initial purging of air from the system while the plunger and vial are mounted in the syringe pump. Specifically, before connecting the tubing to the patient, the syringe pump can be started to force the plunger into the vial. Because any air bubbles that may initially be in the vial would be at the top of the vial, the air bubbles pass into the needle and through the tubing. The air can be vented out of the distal end of the tubing before connecting the tubing to the patient. This is a relatively simple process and avoids the more complex conventional techniques that must be employed when a regular syringe is placed vertically in a syringe pump with a needle projecting downwardly. With such a conventional syringe, the syringe must first be manually held and oriented with the needle pointing upwardly while the syringe plunger is manually pressed slightly to purge the air before inverting the syringe and placing it into the syringe pump.

In the present invention, because the vial stopper post 36 has a relatively short length, and because the stopper includes a cavity 156, a relatively short needle can be employed. Typically, a short, conventional needle may be used rather than a more expensive, longer needle employed in some syringes. In the preferred form, the needle 64 is an 18 gauge needle.

In the preferred form, the tubing 140 is a microbore, polyvinyl chloride tubing with a small internal diameter (approximately 0.050 inch).

The ABBOJECT® brand stopper is normally provided with a threaded post 36. Thus, if desired, the plunger 60 of the present invention may be modified to threadingly engage such a threaded post. To that end, the ribs 124 of the plunger pieces 66 and 68 (FIG. 6) may be replaced with a suitable thread form. With such a construction, the plunger could be pulled in certain optional procedures to establish a suction effect within the vial.

It will be appreciated that the flange 48, which is added to the vial 10, may be located at any appropriate location along the length of the vial, depending upon the structure and size of the syringe pump to be used. However, a number of the newer, conventional syringe pumps typically employ a standard arrangement so that the vial 10 can be provided with the flange 46 at a particular location that will function in a variety of syringe pumps.

It will be appreciated that the capability of the system of the present invention to use glass vials eliminates a intermediate step employed in some conventional procedures wherein the liquid agent is transferred from a glass vial (as provided by the liquid agent supplier) to a plastic syringe. The use of a glass vial is advantageous with those types of liquid agents that are only stable over a long shelf life term in glass (as opposed to thermoplastic containers). However, the plunger system of the present invention may also be employed with a variety of vials, including plastic vials.

It will also be appreciated that the present invention system may be employed with vials having only a single open end and single stopper (as illustrated). This eliminates having to use vials with two open ends and two stoppers. The present invention thus provides a more simple and economical design.

It will be readily apparent from the foregoing detailed description of the invention and from the illustrations thereof that numerous variations and modifications may be effected without departing from the true spirit and scope of the novel concepts or principles of this invention.

What is claimed is:

1. A system for injecting a liquid agent into a patient comprising:

a vial defining an internal chamber having a closed end and an open end, said open end having a stopper slidably mounted therein, said stopper fluidly sealing said internal chamber;

a plunger comprising a substantially annular wall and an end wall mounted on a first end portion of said substantially annular wall, said substantially annular wall and said end wall defining a chamber, said substantially annular wall having a drive end portion mounted on a second end portion thereof, said drive end portion constructed to engage said stopper, said drive end portion of said substantially annular wall constructed to enter said open end of said vial; and a hollow piercing needle mounted on said plunger within said chamber defined by said substantially annular wall and said end wall, said hollow piercing needle having a piercing end constructed to penetrate said stopper, said hollow piercing needle fluidly connected to a first end portion of a tube, said tube having a second end portion, said substantially annular wall of said plunger defining a channel therethrough at a position spaced from said hollow piercing needle, said tube passing through said channel defined through said substantially annular wall of said plunger, said hollow piercing needle and said tube defining a fluid flow path from said internal chamber to a point external to said internal chamber.

2. The system in accordance with claim 1 in which said plunger comprises two identical, mating pieces.

3. The system in accordance with claim 1, wherein said system further comprises:

a curved guide surface positioned within the substantially annular wall of said plunger, and wherein said tube extends over said curved guide surface prior to passing through said channel defined by said substantially annular wall.

4. A system for injecting a liquid agent into a patient comprising:

a vial defining an internal chamber having a closed end and an open end, said open end having a stopper slidably mounted therein, said stopper fluidly sealing said chamber;

a plunger comprising two mating pieces, each said mating piece defining an aperture having an adjacent lug and a tab having a latching surface, said mating pieces constructed such that one mating piece is received in the aperture of the other mating piece and such that each latching surface engages the lug of the other mating piece, said plunger having a substantially annular wall defining a chamber therein, said substantially annular wall having a drive end portion constructed to engage said stopper, said drive end portion of said substantially annular wall constructed to enter said open end of said vial; and a hollow piercing needle mounted on said plunger within said annular wall, said hollow piercing needle having a piercing end constructed to penetrate said stopper, said hollow piercing needle fluidly connected to a first end portion of a tube, said tube having a second end portion, said second end portion of said tube defining a fluid flow path to a point external said plunger, said hollow piercing needle and said tube defining a fluid flow path from said internal chamber to a point external to said internal chamber.

5. A system in accordance with claim 4, wherein each of said mating pieces further comprises a pin and a bore, and wherein the pin of one mating piece is received in the bore of the other mating piece.

* * * * *